(12) United States Patent  
Higuchi

(10) Patent No.: US 8,445,204 B2  
(45) Date of Patent: May 21, 2013

(54) METHODS OF IDENTIFICATION OF METHYLATION OF CPG

(75) Inventor: Russell Higuchi, Alameda, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 216 days.

(21) Appl. No.: 13/020,710

(22) Filed: Feb. 3, 2011

(65) Prior Publication Data

US 2011/0136120 A1   Jun. 9, 2011

Related U.S. Application Data

(62) Division of application No. 12/181,981, filed on Jul. 29, 2008, now abandoned.

(60) Provisional application No. 60/952,815, filed on Jul. 30, 2007.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

2003/0180779 A1* 9/2003 Lofton-Day et al. .............. 435/6
2005/0202490 A1   9/2005 Makarov et al.

FOREIGN PATENT DOCUMENTS

WO   2005078121 A1   8/2005
WO   PCT2008006237   3/2009

OTHER PUBLICATIONS

Nouzova, M., et al., 2004, "Epigenomic Changes during Leukemia Cell Differentiation: Analysis of Histone Acetylation and Cytosine Methylation Using CpG Island Microarrays", The Journal of Pharmacology and Experimental Therapeutics, 311(3):968-981.
Ochman, Howard, et al., 1988, "Genetic Applications of an Inverse Polymerase Chain Reaction", Genetics, 120:621-623.
Tryndyak, Volodymyr, et al., 2006, "Identification of differentially methylated sites within unmethylated DNA domains in normal and cancer cells", Analytical Biochemistry, 356:202-207.
Yamada, Yoichi, et al., 2004., "A Comprehensive Analysis of Allelic Methylation Status of CpG Islands on Human Chromosome 21q", Genome Research, 14(2):247-266.
Gehring, Mary, et al., 2006, "Demeter DNA Glycosylase Establishes MEDEA Polycomb Gene Self-Imprinting by Allele-Specific Demethylation", Cell, 124:495-506.
Lasken, Roger S., et al., 1984, "The Biochemical Basis of 5-Bromouracil-induced Mutagenesis: Heteroduplex Base Mispairs Involving Bromouracil in G.C-A.T and A.T-G.C Mutational Pathways", The Journal of Biological Chemistry, 259(18):11491-11495.
Morales-Ruiz, Teresa, et al., 2006, "Demeter and Repressor of Silencing 1 encode 5-methylcytosine DNA glycosylases", Proceedings of the National Academy of Sciences of the United States of America, 103 (18):6853-6858.
Lu, Jing, et al., 2004, "Unique ligation properties of eukaryotic NAD+-dependent DNA ligase from Melanoplus sanguinipes entomopoxvirus", Biochimica et Biophysica Acta, 1701(1-2):37-48.
Stewart, F. J., et al., 1998, "Dependence of McrBC Cleavage on Distance between Recognition Elements", Biological Chemistry, 379:611-616.
Laird, P. The Power and the Promise of DNA Methylation Markers. Nature Reviews Cancer (2003), v. 3, p. 253-266.

* cited by examiner

*Primary Examiner* — Theresa E Strzelecka
(74) *Attorney, Agent, or Firm* — Olga Kay

(57) ABSTRACT

The present invention relates to the materials and methods for the identification of methylated nucleotides in samples of genomic DNA. The present invention also relates to methods of diagnosis of specific conditions by identification of specific methylated nucleotides.

3 Claims, 3 Drawing Sheets

A

*alternative to ligation: chain extension and strand-displacement synthesis by DNA polymerase

B

*alternative to ligation: mismatch extension and strand-displacement synthesis by DNA polymerase

METHODS OF IDENTIFICATION OF METHYLATION OF CPG

FIELD OF THE INVENTION

The present application is a divisional of the application Ser. No. 12/181,981, filed on Jul. 29, 2008, which claims priority to the provisional application Ser. No. 60/952,815, filed on Jul. 30, 2007.

BACKGROUND OF THE INVENTION

The detection of 5-methyl cytosine in human DNA, usually at CpG dinucleotides, is important diagnostically because the methylation at such cytosines, particularly at gene control sequences, (e.g. promoter sequences) is frequently associated with the onset of cancer. This so-called epigenetic (since it is not in the usual sense heritable) modification of DNA is also important in development and frequently results in gene silencing. In cancer, the epigenetic change is aberrant and can result in the silencing of genes involved in the suppression of tumor formation, or alternatively the activation of genes involved in oncogenesis.

Current widely used methods to detect such DNA modification use treatment of DNA with the chemical bisulfite and have disadvantages with respect to performing a robust diagnostic assay. Among these are high complexity, the lengthy amount of time required, lack of reproducibility and significant loss of the DNA to be detected. In addition, the use of bisulfite is incompatible with the use of uracil-n-glycosylase in the control of carryover PCR product contamination. There is need for a method without these disadvantages.

At the same time there is a need for methods that detect such DNA modifications with high sensitivity and in the presence of high background levels of the same DNA sequence, unmodified. In a tumor, not all the cells contain DNA that is methylated at the sequence of interest—in fact, the majority of cells may not. Furthermore, in the case of early detection of cancer using either disseminated tumor cells or tumor DNA that can be found in the bloodstream, the vast majority of DNA is not methylated at the sequence of interest. At most, only a small percent of copies of that sequence may be methylated. The concentration of such sequences may be less than a single copy per milliliter of sample volume. The need for both high sensitivity and high specificity in detection is both clear and difficult to obtain by previous methods.

SUMMARY OF THE INVENTION

In certain embodiments, the present invention comprises a method of detecting methylated DNA at a specific locus in a sample, comprising: (a) treating the sample with a methyl-active cleavage method that cleaves DNA at a consistent site in the presence of methylated DNA at the specific locus in the sample, (b) adding primers which compliment DNA at or near the specific locus, (c) subjecting the sample to a polymerase chain reaction and generating an amplification product when there is methylated DNA at the specific locus in the sample, and (d) detecting the presence of the amplification product, indicating the presence of methylated DNA at the specific locus in the sample.

In certain embodiments, the present invention comprises a method of detecting methylated DNA at a specific locus in a sample, comprising: (a) treating the sample with a methyl-active method that results in base excision at a consistent site in the presence of methylated DNA at the specific locus in the sample, (b) altering the DNA sequence at the site of cleavage or base excision, (c) adding primers and/or probes which compliment DNA at or near the specific locus and at least one of which is capable of specifically recognizing the altered DNA sequence, (d) subjecting the sample to a polymerase chain reaction and generating an amplification product and/or probe signal when there is methylated DNA at the specific locus in the sample, and (e) when amplification product or probe signal is specifically generated, detecting the presence of the amplification product, indicating the presence of methylated DNA at the specific locus in the sample.

In certain embodiments, the present invention comprises methods of diagnosing certain conditions by the detection of methylated cytosine at a specific locus in genomic DNA samples.

In certain embodiments, the invention comprises methods of detecting methylated DNA at a specific locus in a sample, comprising treating the sample with a methyl-active cleavage method that cleaves DNA at a consistent site in the presence of methylated DNA at the specific locus in the sample, adding primers which compliment DNA at or near the specific locus, subjecting the sample to a polymerase chain reaction and generating an amplification product when there is methylated DNA at the specific locus in the sample, and detecting the presence of the amplification product, indicating the presence of methylated DNA at the specific locus in the sample.

In further embodiments, the sample comprises genomic DNA.

In further embodiments, the specific locus is a promoter region of a known gene. In further embodiments, the sample comes from a patient, and the presence of methylated DNA at the promoter region of the known gene indicates the presence cancerous cells in the patient.

In further embodiments, the methyl-active cleavage method that cleaves DNA at a consistent site in the presence of methylated DNA is a methyl-active restriction enzyme. In further embodiments, the methyl-active cleavage method that cleaves DNA at a consistent site in the presence of methylated DNA is treatment with 5-methyl deoxycytidine glycosylase/lyase, treatment with 5-methyl deoxycytidine glycosylase followed by a separate apurinic/apyrimidinic lyase (or separate apurinic/apyrimidinic endonuclease) or treatment with 5-methyl deoxycytidine glycosylase followed by alkaline hydrolysis.

In certain embodiments, the present invention comprises methods of detecting cancer in a patient by detecting methylated DNA at a specific locus in a sample from the patient, comprising treating the sample with a methyl-active cleavage method that cleaves DNA at a consistent site in the presence of methylated DNA at the specific locus in the sample, adding primers which compliment DNA at or near the specific locus, subjecting the sample to a polymerase chain reaction and generating an amplification product when there is methylated DNA at the specific locus in the sample, detecting the presence of the amplification product, indicating the presence of methylated DNA at the specific locus in the sample, and detecting cancer in the patient from the presence of the amplification product.

In certain embodiments, the sample comprises genomic DNA. In certain embodiments, the specific locus is a promoter region of a known gene. In certain embodiments, the methyl-active cleavage method that cleaves DNA at a consistent site in the presence of methylated DNA is a methyl-active restriction enzyme. In certain embodiments, the methyl active cleavage method that cleaves DNA at a consistent site in the presence of methylated DNA is treatment with 5-methyl deoxycytidine glycosylase/lyase, treatment with 5-methyl deoxycytidine glycosylase followed by a separate apurinic/ apyrimidinic lyase (or separate apurinic/apyrimidinic endonuclease) or treatment with 5-methyl deoxycytidine glycosylase followed by alkaline hydrolysis.

In certain embodiments, the present invention comprises methods of detecting cancer in a patient by detecting methylated DNA at specific locus in genomic DNA in a sample from the patient comprising treating the genomic DNA with a methyl-active restriction enzyme to create a cleavage product, adding primers which compliment DNA at or near the specific locus, subjecting the sample to a polymerase chain reaction to obtain an amplification product when there is methylated DNA at the specific locus, detecting the presence of the amplification product which indicates the presence of methylated DNA at the specific locus, and detecting cancer in a patient by detecting the presence of the amplification product.

In certain embodiments, the specific locus is a promoter region of a known gene. In certain embodiments, the methyl-active restriction enzyme is *E. coli* McrBC. In certain embodiments, the method further comprises the steps of creating blunt ends on the cleavage product, ligating the ends of the cleavage product to create a closed circle of the cleavage product, and the primers are oriented such that the amplification product can only result from a closed ligated circle of the cleavage product.

In certain embodiments, the present invention comprises methods of detecting cancer in a patient by detecting methylated DNA at specific locus in genomic DNA in a sample from the patient comprising treating the genomic DNA with a methyl-active restriction enzyme to create a cleavage product, creating blunt ends on the cleavage product, ligating the ends of the cleavage product to create a closed circle of the cleavage product, adding primers which compliment DNA at or near the specific locus wherein the primers are oriented such that an amplification product can only result from a closed ligated circle of the cleavage product, subjecting the sample to a polymerase chain reaction to obtain an amplification product, detecting the presence of the amplification product which indicates the presence of methylated DNA at the specific locus, and detecting cancer in a patient by detecting the presence of the amplification product.

DETAILED DESCRIPTION OF THE INVENTION

Definitions

The term "amplicon" refers to a double-stranded DNA molecule generated as the result of an amplification reaction, such as the Polymerase Chain Reaction.

As used in the present invention, the term "CpG site" refers to the cytosine and guanisine dinucleotide which may be methylated at the cytosine in some genomic DNA molecules. Typically, the CpG dinucleotide is present within a larger nucleic acid sequence.

The phrase "methyl-active restriction enzyme" in the present invention refers to a restriction enzyme which only cleaves DNA when methylated cytosine is present in the DNA. Different such enzymes may require the methylated cytosine to be at a specific site.

The phrase "methyl-active cleavage" in the present invention refers to a cleavage of nucleic acid which occurs only in the presence of a methylated nucleic acid. In the present invention, methods of methyl-active cleavage include, but are not limited to, the use of methyl-active restriction enzymes.

In the present invention, the term "5-methyl deoxycytidine glycosylase/lyase" refers to an enzyme, both a glycosylase and a lyase, which is active in the presence of a 5-methyl deoxycytidine (Morales-Ruiz T, Ortega-Galisteo A P, Ponferrada-Marin M I, Martinez-Macias M I, Ariza R R, Roldan-Arjona T. *Proc Natl Acad Sci USA*. (2006) 103(18):6853-8; Gehring M, Huh J H, Hsieh T F, Penterman J, Choi Y, Harada J J, Goldberg R B, Fischer R L. *Cell*. (2006) 124(3):495-506). The glycosylase activity of the 5-methyl deoxycytidine glycosylase/lyase typically breaks the N-glycosidic bond between 5-methyl deoxycytidine and ribose of DNA. The lyase activity, also known as apurinic/apyrimidinic (AP) lyase, cleaves the DNA backbone 3' to the abasic sugar by a beta-elimination reaction.

Nucleic acid—In the present invention, the phrase "nucleic acid" may refer to any natural or synthetic nucleic acid, including, but not limited to, single-stranded and double-stranded nucleic acids, DNA, RNA, zDNA, synthetic nucleotide analogs, and peptide-linked synthetic nucleotides.

Gene of Interest—In the present invention, the term "gene of interest" may refer to any coding or non-coding region present in a genomic sequence that a researcher or clinician examines for methylation.

Promoter region—In the present invention, a "control region" may be any portion of a nucleic acid near a gene of interest that is not necessarily included within the gene. A controlling region may or may not have a direct regulatory effect on the expression of the gene of interest. A controlling region is typically a region which may have a methylated 5-deoxycytidine in certain cells where the expression of the gene of interest is affected.

Methyl-Active Cleavage

The present invention encompasses several methods for methyl-active cleavage. Any method that cleaves DNA in the presence of methylated CpG, but does not cleave DNA in the absence of methylated DNA can be used in the present invention. Methods include, but are not limited to, methyl-active restriction enzymes, such as McrBC (Stewart, F. J. and Raleigh E. A. (1998) *Biol. Chem.* 379: 611-616.) and 5-methyl cytidine glycosylase combined with lyase.

Amplification Methods

A variety of amplification methods are envisioned by the present invention, including, but not limited to, the polymerase chain reaction (PCR), ligase chain reaction, and rolling circle replication.

Detection Methods

Several methods of detecting specific species of amplification product are considered by the present invention. Methods of detection include, but are not limited to, incorporation and detection of labels, probe capture methods, Taqman assays, electrophoretic methods, and hybridization methods. Labels include, but are not limited to, radio-labelled nucleotides, fluorophores, quantum dots, biotin-conjugated nucleotides, and chromogenic enzymes.

A variety of methods may be used which couple detection of methylated CpG at a specific locus and amplification. For example, a genomic sample may be cleaved through a methyl-active enzyme which is active in the presence of methylated CpGs. A segment of DNA resulting from such cleavage may be subjected to enzymatic "blunting" of the ends, to which an oligonucleotide adapter of a known sequence is ligated. The sample may then have two primers added, one of which hybridize to a region near the specific locus, and the second of which hybridizes to the known sequence on the oligonucleotide adapter. The aforementioned example is illustrated below in FIG. 1.

In certain embodiments, the invention may be practiced as follows. A specifically detectable DNA sequence alteration may be produced enzymatically near the sites of two 5-methyl cytosines in DNA. As diagrammed in FIGS. 1 and 2 below, the restriction enzyme *E. coli* McrBC may specifically recognize and cleave dsDNA near 5-methyl dC residues that are preceded directly by dA or dG (purines=Pu). These include 5-methyl dC's that precede dG residues to form CpG dinucleotides, the major site of methylation in mammalian DNA. If the dC residue is not methylated, no cleavage takes place. For this reason McrBC is described as "methyl-active," as opposed to "methylation sensitive," which describes a larger known class of restriction enzymes for which the opposite is true, that is, an unmethylated target sequence is cleaved while a methylated target sequence is not.

Strictly speaking, to cleave DNA, McrBC typically requires two Pu$^m$C sites spaced from 55 bp to up to 3 kbp apart. The cleavage site would be approximate 30 bp from one of the two Pu$^m$C sites. Because sites of DNA methylation involved in gene regulation contain a high density of methylated CpG dinucleotides, the situation diagrammed in FIGS. 1 and 2 that results in the production of a novel methylation-specific DNA fragment would likely occur. Note that the cleavages do not need to be between the recognition sites, but are diagrammed that way for example. When it does occur, the creation of a methylation-specific sequence alteration at the cleavage site(s) is possible. For example, in both FIGS. 1 and 2 below, the methylation-specific DNA fragment is treated as described in the references to create ligatable fragment ends. If, as in FIG. 1, the DNA fragment is then allowed to cyclize in the presence of DNA ligase, a covalently-closed DNA circle may be created. The ligated junction site and sequence may be determined empirically using samples containing methylated target genes from, for example, DNA from human tumors. This may be done using DNA cloning and sequencing. Once known, specific DNA primers may be designed and synthesized for PCR that would amplify a specific DNA product as diagrammed, with one primer specific for the novel junction sequence. Amplification following cyclization of a DNA fragment is referred to as "inverse" PCR (Ochman H, Gerber A S, Hard D L. *Genetics*. (1988) 120(3): 621-623.). Alternatively, as in FIG. 2, a synthetic, dsDNA fragment known as a "linker" or as an "adapter" can be ligated to either or both of the fragment ends. Since all the sequences shown will be known, a primer for PCR can be designed that specifically targets the junction sequence between the methylation-specific fragment and the linker. To increase specificity (as many different fragments will also now contain the linker sequence), "nested" PCR may be done as diagrammed.

It would also be possible to target the novel junction sequences with fluorescent oligonucleotide probes compatible with PCR (e.g., Taqman probes), and use flanking PCR amplification primers. However, targeting the novel sequence with a PCR primer instead of a probe has the advantage in the situation where the methylation-specific target is a minority sequence in the background of an amplifiable alternative (which is likely if the diagnostic application is early cancer detection from DNA found in bodily fluids such as serum or plasma—the majority of the DNA is "wild type" and not methylated). If both are amplified, the signal that can be generated by the probe is reduced. If only the methylation-specific target is amplified, signal-to-background is enhanced.

With flanking primers, and using inverse PCR, it is possible that there may not be an amplifiable alternative. In the absence of significant methylation in the region of interest the cleaved fragment will be large and the amplification primers may be placed such that, in the absence of methylation, the amplification product will be too large to amplify efficiently.

Other nucleic acid amplification methods, such as SDA, should be adaptable to detect the methylation-specific sequence change as well.

In certain embodiments, the invention may be practiced as follows. As diagrammed in FIG. 3, the enzyme 5-methyl deoxycytidine glycosylase/lyase can specifically recognize and remove a 5-methyl cytosine nucleotide from dsDNA (in particular from a CpG dinucleotide), leaving a one nucleotide gap that is preceded 5' by a nucleotide bearing a 3' phosphate or an $\alpha,\beta$-unsaturated aldehyde (not shown), both of which can be removed using *E. coli* endonuclease IV, leaving a free 3' hydroxyl group suitable for nucleotide chain extension by a DNA polymerase. In FIG. 3A, such a chain extension is performed using a single nucleotide triphosphate (dNTP) that is "mutagenic". That is to say, the dNTP can be inserted efficiently at this position and, when the DNA strand containing the mutagenic nucleotide is subsequently copied by DNA polymerase, a nucleotide is inserted that alters the original base sequence. An example, and not the only example, of this is 5-bromodeoxyuracil nucleotide triphosphate (5-BrdUTP) which can be efficiently inserted opposite a dG residue by a DNA polymerase, particularly in the absence of dCTP. But when copied in the presence of all four natural dNTPs, a dA residue, rather than a dC residue, is preferentially inserted (Lasken R S, Goodman M F. *J Biol Chem*. (1984) 259(18): 11491-5). To prevent an analog from being removed once incorporated, the polymerase can lack 3' exonuclease proofreading activity. Once such an analog is incorporated, it can be ligated to the 5' phosphate at the gap. Alternatively, the dNTP analog can be removed and chain extension from the 3' OH of the incorporated nucleotide analog can be made to proceed with DNA polymerase (lacking 3' exonuclease) and the four natural dNTPs along with strand-displacement of the preexisting, annealed DNA strand.

This is followed by the separation of the two DNA strands by, for example, heat denaturation, and the primed synthesis by a DNA polymerase of copies of the strand containing the mutagenic nucleotide analog. Because of the analog, copies are made that have an altered nucleotide base sequence. Once a genomic methylation site and surrounding sequence is identified, model experiments can be performed to identify the specific sequence alterations produced by this procedure. Such an altered sequence can be efficiently and sensitively detected by primer-directed DNA amplification (e.g., PCR). PCR is well-known to discriminate against single-base mismatches to a primer, in particular against mismatches at the 3' terminus of the primer; such mismatches can be designed into a primer made for a given assay.

Alternatively, as diagrammed in FIG. 3B, a DNA polymerase (lacking 3' exonuclease proofreading activity) and dGTP, dATP or dTTP alone can be provided. In the absence of dCTP a mismatched nucleotide base can be forced to incorporate opposite dG. This can be promoted by the presence of $Mn^{++}$ and the use of misincorporation prone polymerases such as viral reverse transcriptases. The single dNTP provided should not be the one expected to incorporate one base upstream of the 5-methyl dC replacement, as a nick or gap at this position might translate to the replacement site, giving a false positive result. Efficient, enzyme-mediated ligation of a nucleotide base mismatched to dG can also be made to take place (Lu J, Tong J, Feng H, Huang J, Afonso C L, Rock D L, Barany F, Cao W. *Biochim Biophys Acta*. (2004) 1701(1-2): 37-48.). Or, instead of ligation taking place, once misincorporation has been allowed to take place, the remaining three natural dNTPs can be provided and, in the absence of 3' exonuclease proofreading activity, efficient extension from the incorporated, mismatched nucleotide can be made to occur. As above, this results in a specifically knowable, amplifiable and detectable sequence change.

EXAMPLES

The following are prophetic, and do not represent actual experiments.

Example 1

A sample of fluid may be taken from a patient. Genomic DNA may be extracted from the patient sample using known methods.

The genomic DNA extracted is then treated with a restriction enzyme that is active in the presence of methylated cytosine in CpG sites, yielding an enzyme-treated sample. The enzyme-treated sample is then combined with a linker which is ligated to the ends of molecules cleaved by the restriction enzyme.

The mixture is combined with a primer which hybridizes to a sequence near a promoter region of a gene of interest, and a second primer which hybridizes to the linker which is ligated to the ends of the molecules cleaved by the restriction enzyme. Using the primer and the second primer, the mixture may then be subjected to an amplification reaction, such as PCR. When specific CpG sites are methylated, a genomic DNA molecule is cleaved, a linker is ligated, and a specific amplicon is generated from the amplification reaction. In the absence of the specific methylated CpG, the specific amplicon is not generated.

The specific amplicon may then be detected through a variety of known means. If the specific amplicon is detected, indicating the methylated state of the specific CpG site, then a specific neoplasmic state may be indicated and diagnosed.

Example 2

In a further example, a solid tumor biopsy may be obtained from a patient. Established techniques may be used to extract genomic DNA from the solid tumor biopsy to yield a sample.

Figure 1:
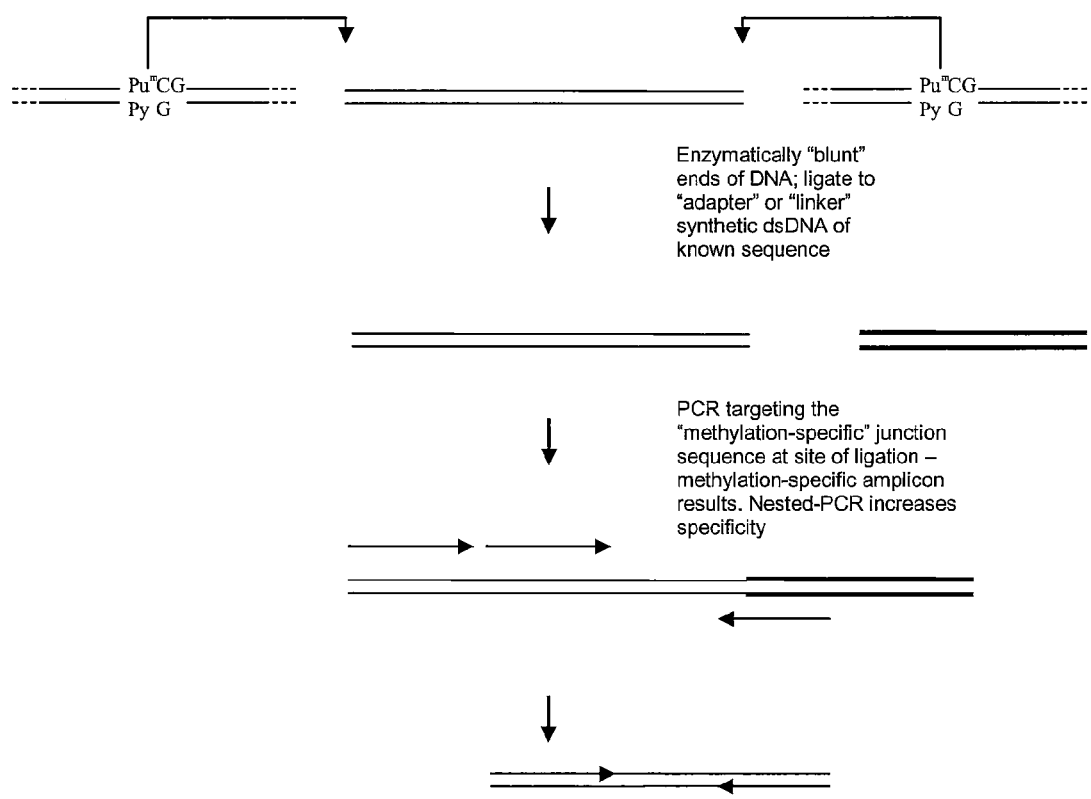
FIG. 1 illustrates a method of amplification detection. The illustrated method employs the ligation of a specific linker, and the use of primers which hybridize to the linker and the excised DNA. Nested primers within the sequence of the excised DNA increase the specificity of the amplification and detection.
Figure 2:
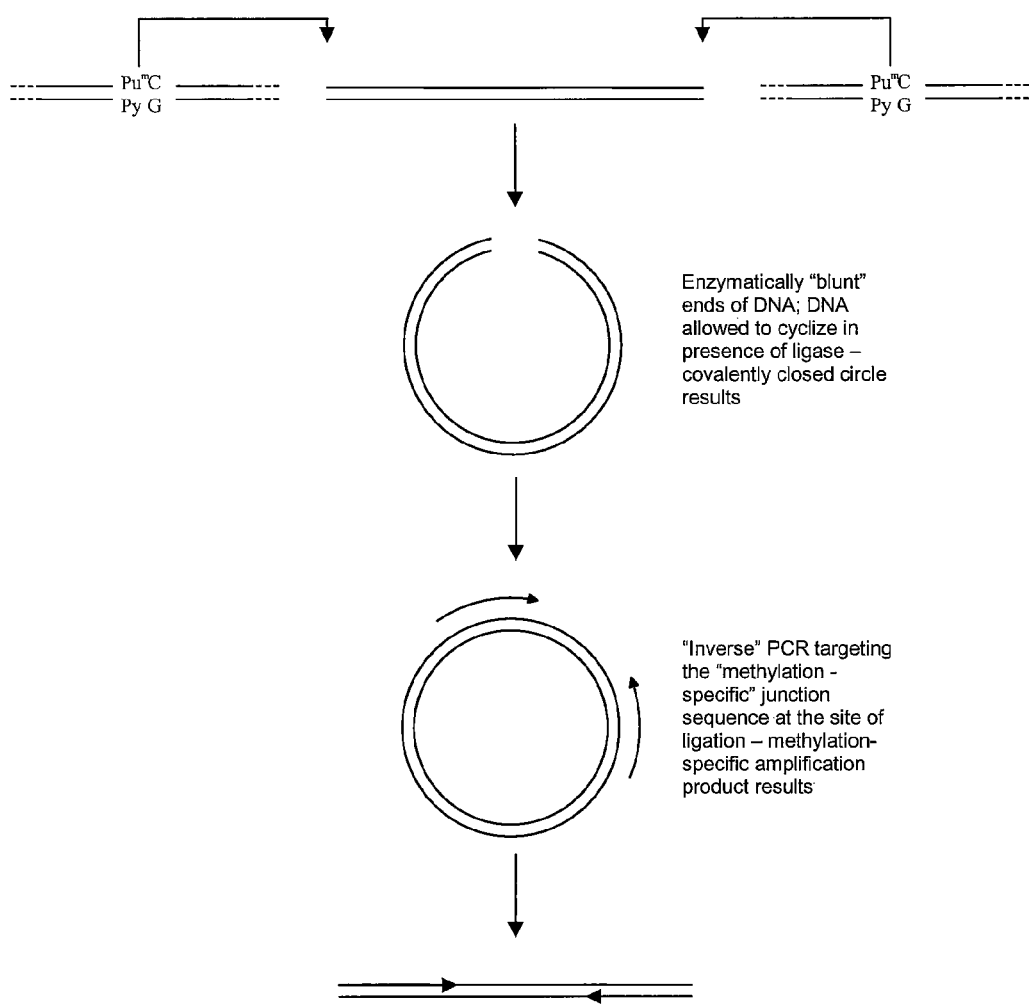
FIG. 2 illustrates another method of amplification and detection using "inverse" PCR. Following excision, the excised DNA fragment is cyclized, and primers which amplify an amplicon over the juncture of ligation are employed to amplify and detect successful cleavage of the DNA.
Figure 3:
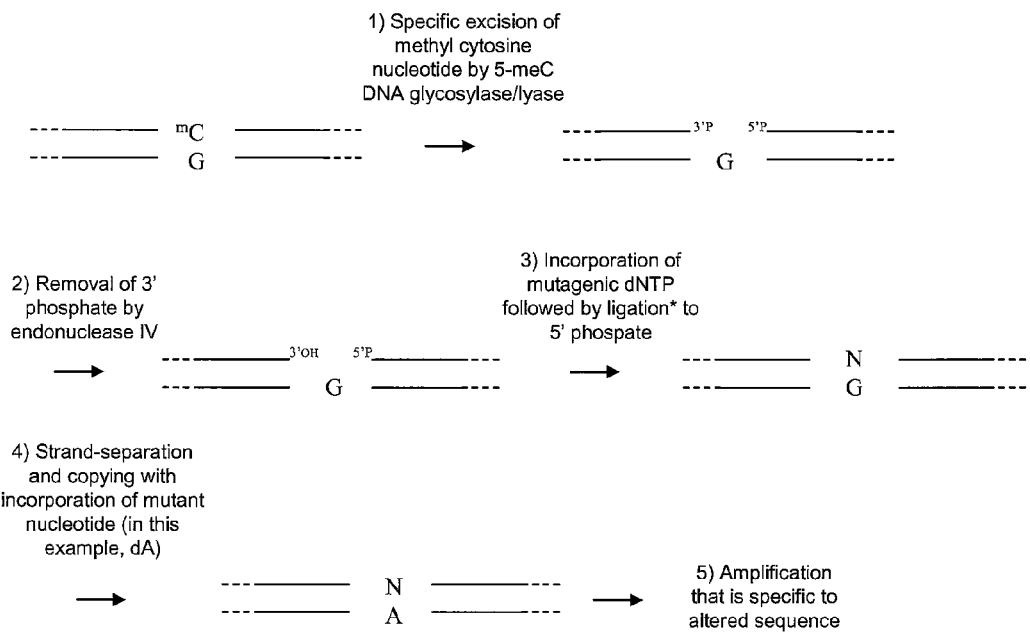
FIG. 3 illustrates another method of amplification and detection using nucleotide excision and mutagenesis. Using a glycosylase specific to 5-methyl cytidine, nucleotide excision is initiated. The excised nucleotide can be replaced by a mutagenic analog (A), or by a misincorporated natural nucleotide (B). In either case, copying by DNA polymerase of the modified DNA strand results in a sequence alteration that is specifically amplifiable and detectable by, for example, PCR.
Figure 3:
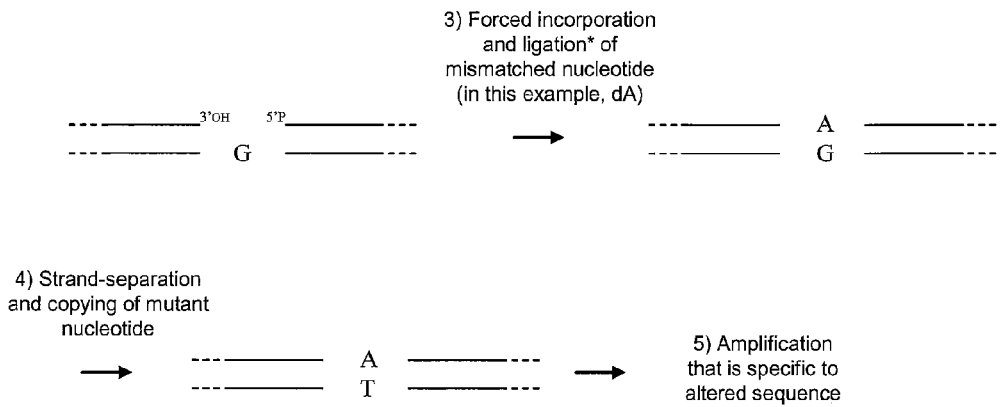

The genomic DNA sample is then treated with a restriction enzyme that is active in the presence of methylated cytosine in CpG sites, yielding an enzyme-treated sample. The enzyme-treated sample may be then treated in a matter which creates blunt-ended double-stranded DNA. This sample may then be subsequently treated with a ligase, creating circular DNA from short pieces of DNA. This example is illustrated below in FIG. 2.

The sample may then be combined with a set of primers which hybridize to sequences near a genomic sequence of interest which, when certain sites near a genomic sequence of interest are cleaved and ligated into a certain circular DNA, generate an amplicon only possible when the certain circular DNA is present. The sample and set of primers may be subjected to an amplification reaction, generating a specific amplicon when CpG sites near the genomic sequence of interest are methylated.

The specific amplicon may be detected, indicating that the solid tumor from which the biopsy was taken was of a specific type of tumor indicated by the methylation of CpG sites near the genomic sequence of interest.

Example 3

In a further example, a solid tumor biopsy may be obtained from a patient. Established techniques may be used to extract genomic DNA from the solid tumor biopsy to yield a sample.

The genomic DNA sample is then treated with a combined 5-methyl cytosine glycosylase/lyase that is active in the presence of methylated cytosine in CpG sites or a 5-methyl cytosine glycosylase that is active in the presence of methylated cytosine in CpG sites followed by a separate AP lyase or AP endonuclease, yielding an enzyme-treated sample with gaps in its double stranded DNA. The enzyme-treated sample may be then treated in a manner that allows the gaps to be filled by a nucleotide with different base-pairing specificity than dC.

The sample is combined with a primer which hybridizes to a sequence in a cancer-related gene of interest, and a second primer which hybridizes specifically to a now mutated sequence near the first primer. In certain embodiments, for the greatest specificity in PCR, the 3' nucleotide or the 3' penultimate nucleotide of the second primer is opposite the mutated base. Using the primer and the second primer, the mixture may then be subjected to an amplification reaction, such as PCR. When specific CpG sites are methylated, a specific amplicon is generated from the amplification reaction. In the absence of the specific methylated CpG, the specific amplicon is not generated.

The specific amplicon may then be detected through a variety of known means. If the specific amplicon is detected, indicating the methylated state of the specific CpG site, then a specific neoplasmic state may be indicated and diagnosed.

The invention claimed is:

1. A method of detecting methylated DNA at a specific locus in a sample, comprising:
    treating the sample with 5-methyl deoxycytidine glycosylase/lyase,
    adding primers which complement DNA at or near the specific locus,
    subjecting the sample to a polymerase chain reaction and generating an amplification product when there is a successful methyl-active cleavage, but no amplification when there is no successful cleavage, and
    detecting the presence of the amplification product, indicating the presence of methylated DNA at the specific locus in the sample.

2. The method of claim 1, wherein the sample comprises genomic DNA.

3. The method of claim 1, wherein the specific locus is a promoter region of a known gene.

* * * * *